United States Patent
Delka et al.

(10) Patent No.: US 10,492,960 B2
(45) Date of Patent: *Dec. 3, 2019

(54) DIAPER SYSTEM AND FLAP

(71) Applicant: ACT Holding, LLC, Overland Park, KS (US)

(72) Inventors: Ryan K. Delka, Fort Collins, CO (US); Bret Delka, Fort Collins, CO (US); Joseph C. Long, Olathe, KS (US)

(73) Assignee: Act Holding, LLC, Olathe, KS (US)

(*) Notice: Subject to any disclaimer, the term of this patent is extended or adjusted under 35 U.S.C. 154(b) by 0 days.

This patent is subject to a terminal disclaimer.

(21) Appl. No.: 15/682,701

(22) Filed: Aug. 22, 2017

(65) Prior Publication Data

US 2018/0049927 A1    Feb. 22, 2018

Related U.S. Application Data

(60) Provisional application No. 62/378,023, filed on Aug. 22, 2016.

(51) Int. Cl.
*A61F 13/494* (2006.01)
*A61F 13/49* (2006.01)
(Continued)

(52) U.S. Cl.
CPC ........ *A61F 13/494* (2013.01); *A61F 13/4946* (2013.01); *A61F 13/49058* (2013.01);
(Continued)

(58) Field of Classification Search
CPC .............. A61F 13/494; A61F 13/49058; A61F 13/539; A61F 13/49001; A61F 13/493;
(Continued)

(56) References Cited

U.S. PATENT DOCUMENTS 4,559,051 A   12/1985 Hanson et al.
4,892,598 A   1/1990  Stevens et al.
(Continued)

FOREIGN PATENT DOCUMENTS

WO   2016205756   12/2016
WO   2017058165   4/2017

OTHER PUBLICATIONS

MamaBanana's Adventures, "GMD Wprkhorse Fitted Review; Prepping Natural Fiber" Jan. 30, 2015. http://mamabananasadventures.com/workhorse-fitted-cloth-diaper-review.html. (Year: 2015).*
(Continued)

*Primary Examiner* — Tatyana Zalukaeva
*Assistant Examiner* — Gabriella E Burnette
(74) *Attorney, Agent, or Firm* — Hovey Williams LLP

(57) ABSTRACT

A diaper insert has a liquid impermeable external surface, an inner surface, and an absorbency area adjacent the inner surface. The absorbency area has at least one absorbent layer. The diaper insert has a distal end, an attachment end, and a midsection between the distal end and attachment end. The midsection has opposing sides that are in general mirror images to one another about a vertical line. A width of the midsection is less than or equal to a width of the attachment end, and a width of the midsection is less than or equal to a width of the distal end.

31 Claims, 12 Drawing Sheets

(51) Int. Cl.
*A61F 13/539* (2006.01)
*A61F 13/505* (2006.01)
*A61F 13/74* (2006.01)

(52) U.S. Cl.
CPC ...... *A61F 13/49466* (2013.01); *A61F 13/505* (2013.01); *A61F 13/539* (2013.01); *A61F 13/74* (2013.01); *A61F 2013/49486* (2013.01)

(58) Field of Classification Search
CPC .......... A61F 13/505; A61F 2013/49486; A61F 2013/5055
See application file for complete search history.

(56) References Cited

U.S. PATENT DOCUMENTS

| | | | |
|---|---|---|---|
| 4,955,880 A | 9/1990 | Rodriquez | |
| 4,961,736 A * | 10/1990 | McCloud | A61F 13/49004 604/385.15 |
| 5,108,385 A | 4/1992 | Snyder | |
| 5,129,718 A | 7/1992 | Futhey et al. | |
| 5,275,592 A | 1/1994 | Grizzath et al. | |
| 5,342,340 A | 8/1994 | Kichefski et al. | |
| 5,371,950 A | 12/1994 | Schumacher | |
| 5,558,734 A | 9/1996 | Sherrod et al. | |
| 5,810,799 A | 9/1998 | Slater | |
| 5,843,065 A | 12/1998 | Wyant | |
| 5,870,840 A | 2/1999 | Geils et al. | |
| 5,878,138 A | 3/1999 | Yacobi | |
| 6,258,076 B1 | 7/2001 | Glaug et al. | |
| 6,491,677 B1 | 12/2002 | Glaug et al. | |
| 6,926,705 B1 * | 8/2005 | Coates | A61F 13/495 604/385.14 |
| 7,128,733 B2 | 10/2006 | Valentin et al. | |
| 7,316,674 B2 | 1/2008 | Infantino et al. | |
| 7,658,731 B2 | 2/2010 | Winqvist | |
| 8,100,876 B1 | 1/2012 | Biondolillo | |
| 8,187,245 B2 | 5/2012 | Winqvist | |
| 8,444,618 B2 * | 5/2013 | Kudo | A61F 13/47218 604/385.101 |
| 8,814,843 B2 * | 8/2014 | Van Bogart | A61F 13/15268 604/385.14 |
| 8,986,271 B1 | 3/2015 | Horne | |
| D737,434 S | 8/2015 | Miller | |
| 9,095,480 B2 | 8/2015 | Breeden et al. | |
| 9,119,749 B2 | 9/2015 | Close et al. | |
| 9,173,799 B2 | 11/2015 | Tanimoto et al. | |
| 9,474,655 B1 | 10/2016 | Biondolillo | |
| 2004/0127864 A1 | 7/2004 | Sugito | |
| 2005/0022291 A1 * | 2/2005 | Coates | A61F 13/49 2/400 |
| 2005/0261658 A1 | 11/2005 | Baumchen | |
| 2007/0197984 A1 | 8/2007 | Richardson et al. | |
| 2008/0114326 A1 | 5/2008 | Roe et al. | |
| 2008/0119816 A1 | 5/2008 | Carstens | |
| 2011/0245791 A1 | 10/2011 | Miller | |
| 2012/0116340 A1 * | 5/2012 | Labit | A61F 13/15268 604/377 |
| 2013/0006208 A1 * | 1/2013 | Close | A61F 13/471 604/385.09 |
| 2013/0274699 A1 * | 10/2013 | Kelley | A61F 13/505 604/385.09 |
| 2014/0188065 A1 | 7/2014 | Defrancesco et al. | |
| 2014/0221954 A1 * | 8/2014 | Wang | A61L 15/40 604/385.14 |
| 2016/0008188 A1 | 1/2016 | Lumaque-Steeman | |
| 2016/0262949 A1 | 9/2016 | Roe et al. | |
| 2016/0279001 A1 * | 9/2016 | Price | A61F 13/84 |
| 2016/0367410 A1 | 12/2016 | Alligood | |
| 2017/0128281 A1 | 5/2017 | Takino et al. | |
| 2017/0239104 A1 | 8/2017 | Jang et al. | |
| 2018/0055698 A1 | 3/2018 | Bishop et al. | |

OTHER PUBLICATIONS

PCT Application No. PCT/US17/47914, International Search Report and Written Opinion, dated Oct. 25, 2017, 12 pages.

* cited by examiner

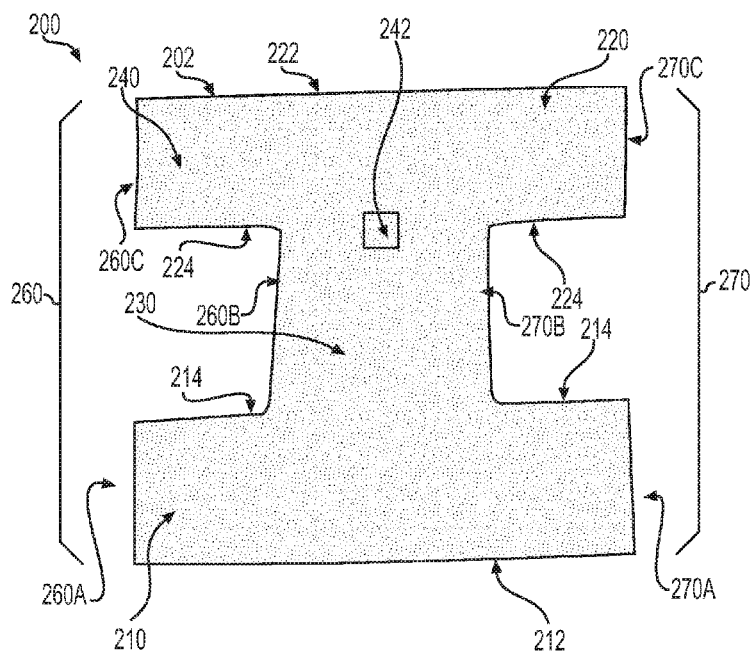
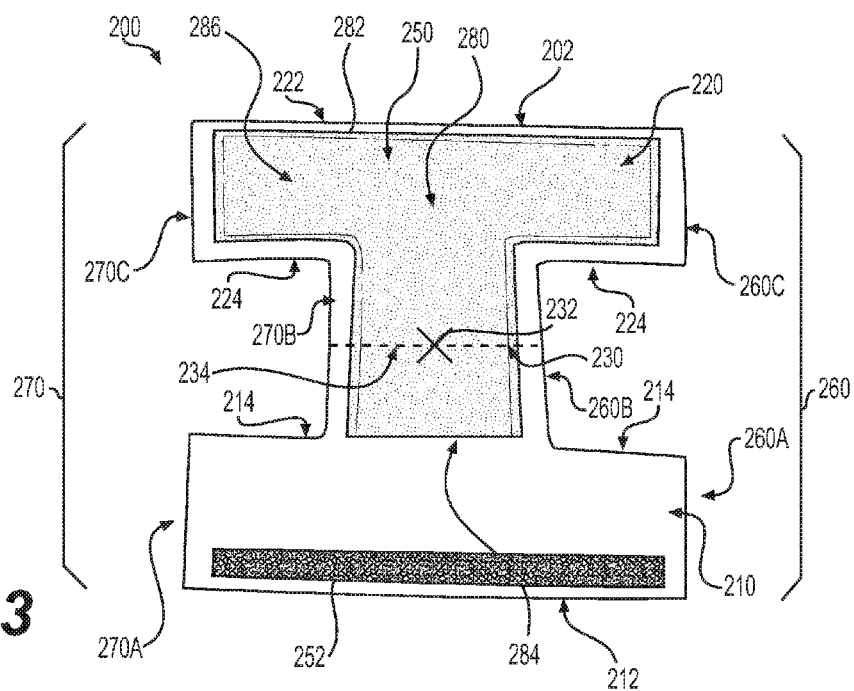

DIAPER SYSTEM AND FLAP

RELATED APPLICATIONS

This application claims priority to U.S. Provisional Patent Application Ser. No. 62/378,023, filed Aug. 22, 2016, the disclosure of which is hereby incorporated in its entirety by reference.

FIELD OF THE INVENTION

The present invention relates to diaper systems and flaps. More specifically, the present invention relates to diaper systems and flaps designed to prevent leakage of bodily fluids.

BACKGROUND

Diaper systems have long been used with children as a way of containing urine and excrement before a child begins to use a toilet. Diapers contain absorbent material to prevent a wearer from soiling outer garments. Diapers may also be utilized by adults or adolescents who are unable to use a toilet or may be incontinent.

BRIEF SUMMARY OF THE INVENTION

The following presents a simplified summary in order to provide a basic understanding of some aspects of the invention. This summary is not an extensive overview of the invention. It is not intended to identify critical elements of the invention or to delineate the scope of the invention. Its sole purpose is to present some concepts of the invention in a simplified form as a prelude to the more detailed description that is presented elsewhere.

In one embodiment, a diaper system has a diaper having a front waist portion for being positioned proximate a wearer's abdominal area when fastened to the wearer and having a front edge, a rear waist portion having a rear edge, a central portion extending from the front waist portion to the rear waist portion, an interior surface, and an outer surface. The diaper system has a flap having an attachment end, a distal end, a midsection between the attachment end and the distal end, an inner surface, and an external surface. The attachment end is coupled to the outer surface. An absorbency area is adjacent the inner surface and has at least one absorbent layer. The midsection has a width that is less than or equal to a width of the distal end.

In another embodiment, a diaper insert has a liquid impermeable external surface, an inner surface, and an absorbency area adjacent the inner surface, the absorbency area having at least one absorbent layer configured to interact with an inner surface of the diaper to form a barrier restricting leakage of bodily fluids. The diaper insert has a distal end, an attachment end, and a midsection between the two. The diaper insert narrows from the attachment end to the midsection. The midsection has a width that is less than or equal to a width of the distal end.

In still another embodiment, an undergarment flap has an external surface, an inner surface adjacent an absorbency area, at least one absorbent layer adjacent the inner surface. The undergarment has an attachment end, a distal end, and a midsection between the attachment end and the distal end. The midsection has opposing sides that are generally mirror images to one another about a vertical line. A width of the midsection is less than or equal to a width of the attachment end and the width of the midsection is less than or equal to a width of the distal end.

In yet another embodiment, a method for minimizing leakage of bodily fluids from exiting a diaper system is provided. A diaper to be worn by a wearer is unfolded. The diaper has a front waist portion for being positioned proximate a wearer's abdominal area, the front waist portion has a front edge. The diaper has a rear waist portion having a rear edge and a central portion extending from the front waist portion to the rear waist portion. The diaper further has an interior surface and an outer surface. Then, a flap is coupled to the outer surface of the diaper. The flap has an attachment end, a distal end, and a midsection between the attachment end and the distal end. The flap further has an inner surface, an external surface, and an absorbency area adjacent the inner surface. The absorbency area has at least one absorbent layer. The flap is then folded up and over into the interior surface of the diaper to form a first fold. The flap is folded again at the midsection to create a folded area and an accordion fold. The flap is folded such that the distal end is proximate the attachment end, and is also proximate the diaper. Lastly, the diaper and the flap are secured to the wearer using side fasteners. The front edge forms a seal with the wearer's abdominal area, and the rear edge forms a seal with the wearer's lower back.

BRIEF DESCRIPTION OF THE DRAWINGS

FIG. 2 is a bottom view of the flap of FIG. 1.

FIG. 3 is a top view of the flap of FIG. 1.

DETAILED DESCRIPTION

Figure 1:
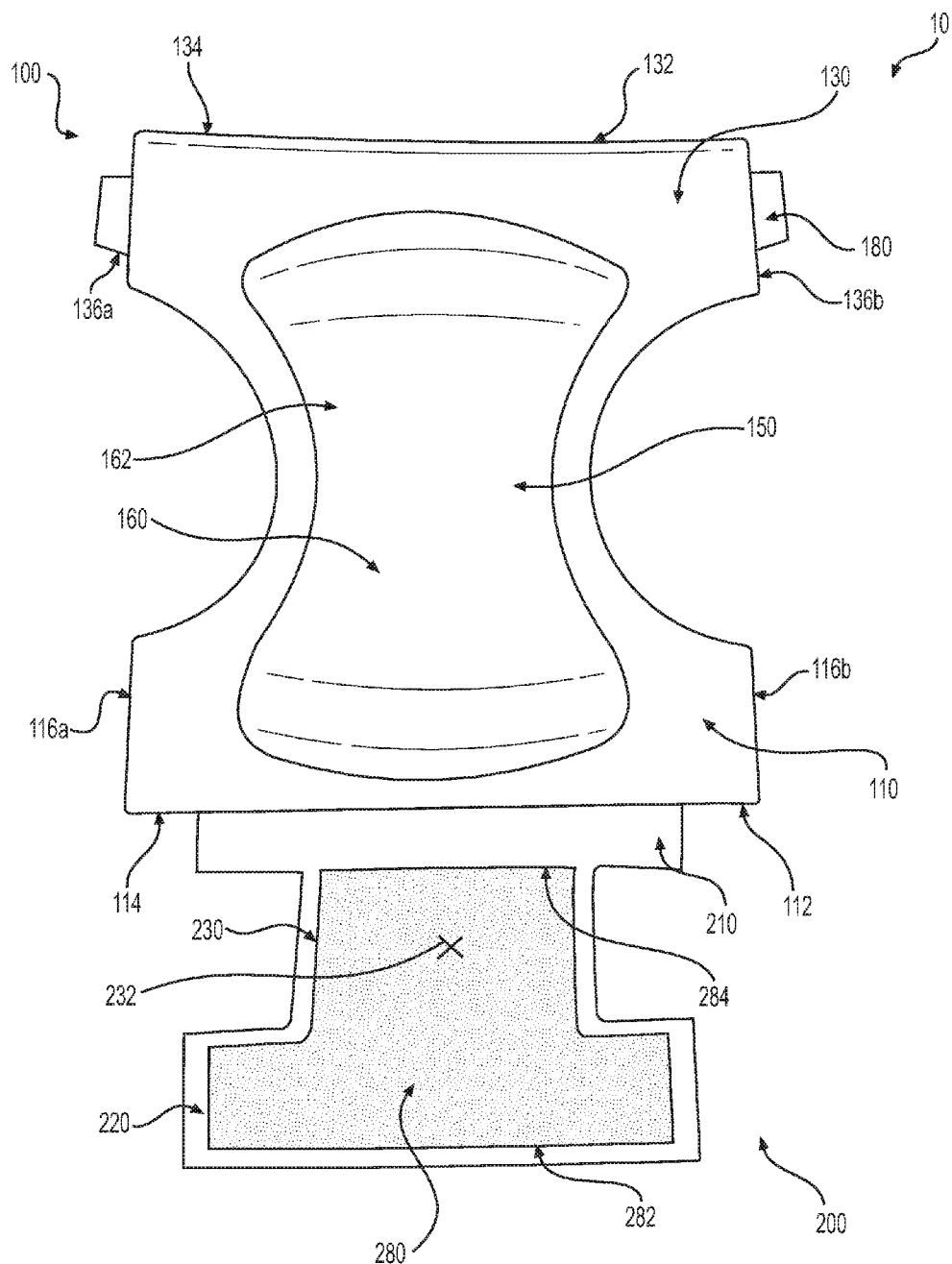
FIG. 1 is a top view of an unfolded diaper and flap according to an embodiment of the invention.

A diaper system 10 having a diaper 100 and a flap 200 may be configured to interact with a wearer to contain bodily fluids. As shown in FIG. 1, the diaper 100 has a front waist portion 110, a rear waist portion 130, a central portion 150, an interior surface 160, and an outer surface 170. The flap 200 has an attachment end 210, a distal end 220, and a midsection 230 between the attachment end 210 and distal end 220. The diaper 100 may generally have an hourglass-shaped planar configuration, as shown in FIG. 1.

The front waist portion 110 may have a front edge 112 defining a top of the front waist portion 114, and opposing sides 116*a*, 116*b* that are generally parallel to each other. The rear waist portion 130 has a rear edge 132 defining a top of the rear waist portion 134, and opposing sides 136*a*, 136*b* that are generally parallel to each other. The central portion 150 is between the front waist portion 110 and the rear waist portion 130. The front waist portion 110 may be positioned proximate the wearer's abdominal area when the diaper 100 is fastened to the wearer, and the rear waist portion 130 may be positioned proximate the wearer's lower back when the diaper 100 is fastened to the wearer.

Side fasteners 180 may be fixed to the rear waist portion 130 proximate each opposing side 136*a*, 136*b*. The side fasteners 180 may be used to attach the rear waist portion 130 to the front waist portion 110. When the side fasteners 180 are engaged, the diaper 100 may be secured to the wearer. The outer surface 170 of the diaper 100 is preferably liquid impermeable. The interior surface 160 may be absorbent, and may consist of at least one absorbent layer 162. The diaper 100 may be disposable, reusable, or constructed from such materials as nonwoven plastic or cotton.

The flap 200 is configured to be coupled to the diaper 100. The flap 200 may be releasably coupled to the diaper 100, or the flap 200 may be securely coupled to the diaper 100. Moreover, the flap 200 may be coupled at a waist band of other types of undergarments, such as training pants, pull-ups, underwear, boxers, or a garter.

Figure 4:
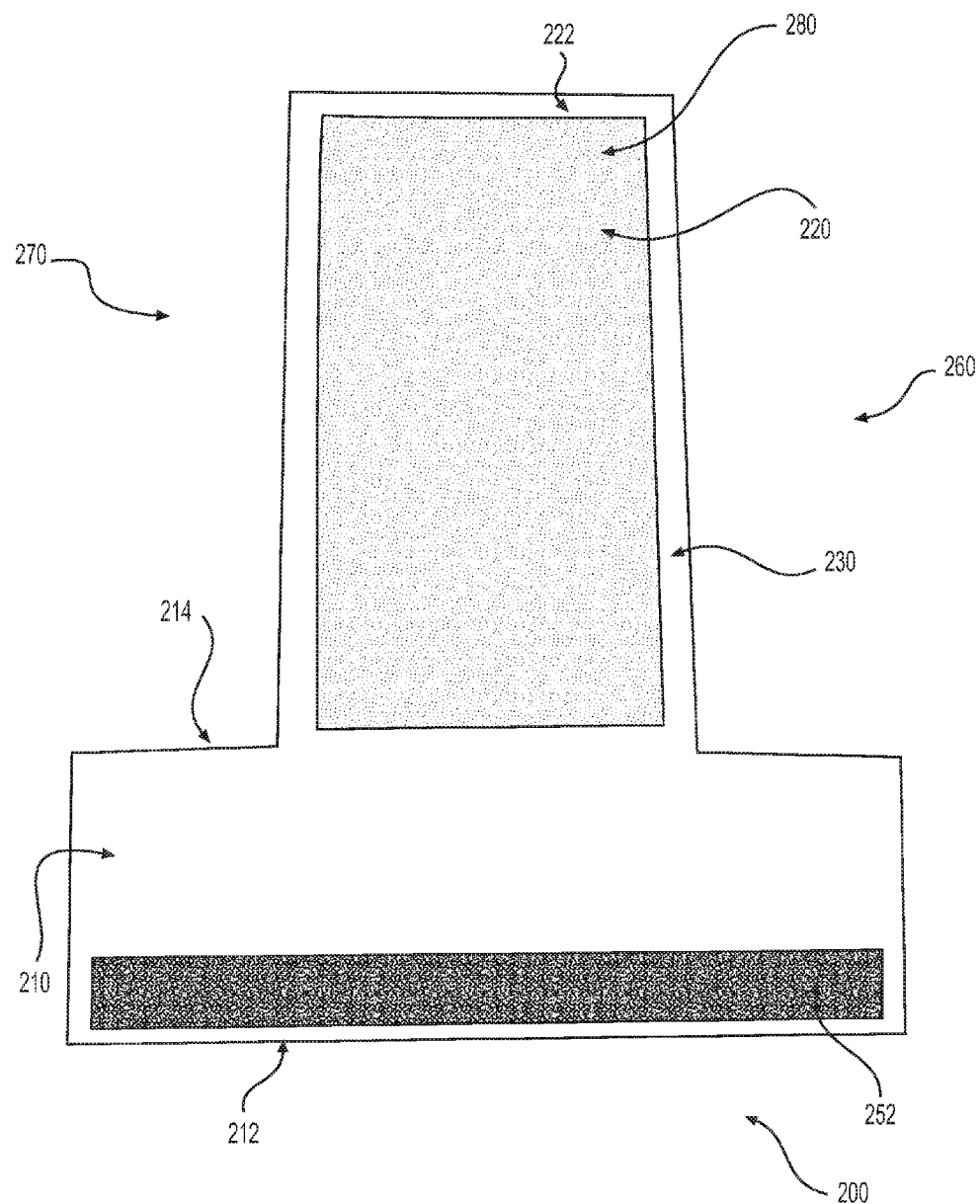
FIG. 4 is a T-shaped flap according to another embodiment of the invention.
Figure 5:
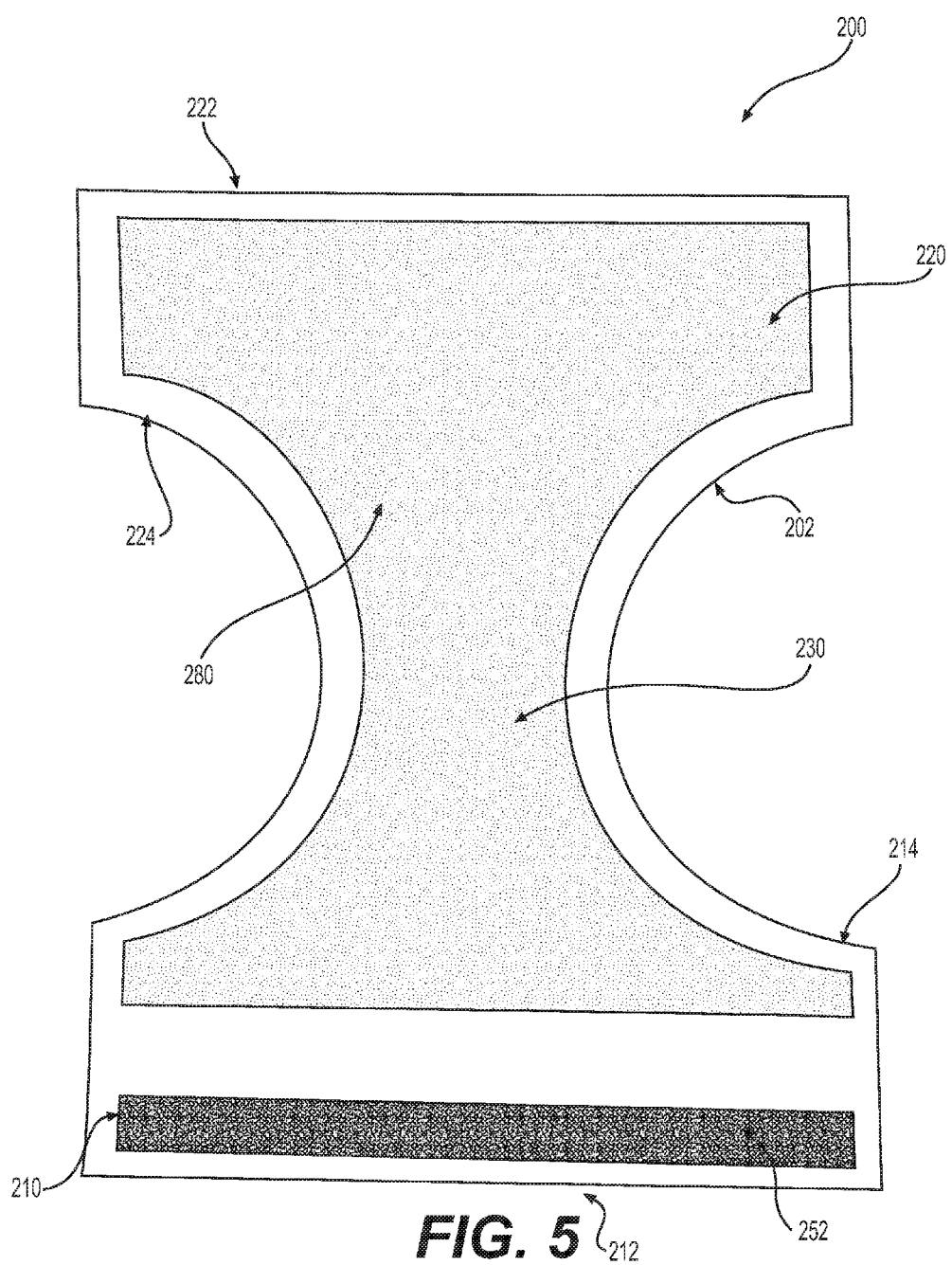
FIG. 5 is an hourglass-shaped flap according to still another embodiment of the invention.

As shown in FIG. 2 and FIG. 3, the attachment end 210 has an edge 212 and a boundary 214 at the midsection 230. The distal end 220 also has an edge 222 and a boundary 224 at the midsection 230. The midsection 230 has a center point 232 that may also be a center point between the distal end 220 and the attachment end 210. There may be a centerline (shown in a dashed line in FIG. 3) at the center point 232. The distal end 220 and the attachment end 210 may be mirror images of each other across the centerline. The flap 200 further has a first side 260 and a second side 270, with a vertical line (not shown) bisecting the flap 200 between the first side 260 and the second side 270. In some embodiments, the two sides 260, 270 may be substantially parallel to one another. Those skilled in the art will appreciate that the attachment end 210 and the distal end 220 may be any shape, including, but not limited to, a trapezoid, rectangle, triangle, and semi-circle. In some embodiments, the attachment end 210 and the distal end 220 may be shaped substantially similar, and may mirror one another. Those skilled in the art will also appreciate that the flap 200 may be any shape. FIG. 4 illustrates an embodiment of the flap 200 wherein the flap 200 is T-shaped. FIG. 5 illustrates an embodiment of the flap 200 wherein the flap 200 has a substantially hourglass configuration. In other embodiments, the flap 200 may be I-shaped, as is shown in FIG. 2 and FIG. 3. The attachment end 210 may have a width approximately equal to a width of the front edge 112.

In the I-shaped embodiments, and as shown in FIG. 2 and FIG. 3, the distal end 220 has a substantially similar width to a width of the attachment end 210. A first and second side 260*a*, 270*a* of the attachment end 210 may be generally parallel to one another. The sides 260*a*, 270*a* may extend from the edge of the attachment end 212 to the boundary of the attachment end 214. The boundary of the attachment end 214 may be generally parallel with the edge of the attachment end 212, and may form a perpendicular angle with the sides 260*a*, 270*a*. The attachment end boundary 214 may abut the midsection 230. In some embodiments, the attachment end boundary 214 may be perpendicular to the midsection 230. A width of the midsection 230 may be defined by a first side 260*b* and a second side 270*b* of the midsection 230. A first and second side 260*b*, 270*b* of the midsection 230 may be parallel to one another throughout the midsection 230. The midsection 230 may abut the distal end boundary 224, which may extend parallel to the edge of the distal end 222. A first and second side 260*c*, 270*c* of the distal end 220 may extend at a perpendicular angle from the distal end boundary 214 toward the edge of the distal end 212, and may be generally parallel each other.

In some embodiments, a width of the flap 200 is the smallest between opposing sides 260*b*, 270*b* of the midsection 230. The width of the flap 200 may vary at different areas of the flap 200. The width of the flap 200 may narrow from the attachment end 210 toward the midsection 230. The width of the flap 200 may similarly narrow from the distal end 220 toward the midsection 230. The width of the flap 200 at the midsection 230 may be less than or equal to a width of the central portion 150 of the diaper 100. In some embodiments, the width of the midsection 230 is less than or equal to the width of the distal end 220. In other embodiments, the width of the midsection 230 is less than or equal to the width of the attachment end 210.

The flap 200 has an external surface 240 and an inner surface 250. The external surface 240 may be liquid impermeable. In some embodiments, for aesthetic purposes, the external surface 240 may have a pattern or other artistic decoration. Further, the external surface 240 may have a wetness indicator. The external surface 240 may have an adhesion area 242 (shown in FIG. 2), and those skilled in the art will appreciate that the adhesion area 242 may utilize an adhesive material, glue, zipper, hook and loop fasteners, or other methods of attachment now known or later discovered. In some embodiments, the adhesion area 242 may utilize a pressure sensitive adhesive material proximate the distal end boundary 224. The adhesion area 242 may be at or proximate to the midsection 230. In some embodiments, the adhesion area 242 may be at the distal end boundary 224 or the attachment end boundary 214. In other embodiments, the adhesion area 242 may be proximate the edge 222 of the distal end 220. The external surface 240 may be secured to itself at the adhesion area 242. The flap 200 would still be able to move relative the adhesion area 242, and the adhesion area 242 may not restrict movement. In some embodiments, the adhesion area 242 is proximate the distal end boundary 224 and adheres to the external surface 240 at the attachment end boundary 214.

The inner surface 250 may be absorbent. In some embodiments, for aesthetic purposes, the inner surface 250 may have a pattern or other artistic decoration. Further, the inner surface 250 may have a wetness indicator. The inner surface 250 may have at least one attachment area 252 proximate the attachment end 210 of the flap 200. The attachment area 252 may be configured to be coupled to the outer surface 170 of the diaper 100. Those skilled in the art will appreciate that the attachment area 252 may utilize an adhesive material, zipper, hook and loop fasteners, safety pins, plastic rivets, roll on glue, or other methods of attachment now known or later discovered. Further, the outer surface 170 of the diaper 100 may be configured to interact with the attachment area 252, and may also utilize an adhesive material, zipper, hook and loop fasteners, or other methods of attachment now known or later discovered. In some embodiments, the attachment area 252 may have a strip of pressure sensitive adhesive material that may be used to couple the flap 200 to the diaper 100. In other embodiments, the attachment area 252 may extend a width of the attachment end 210. In still other embodiments, the flap 200 has multiple attachment areas 252. In some embodiments, the side fasteners 180 may be utilized to secure the flap 200 to the diaper 100. Alternately, the flap 200 may be secured to the outer surface 170 by an adhesive material.

The attachment area 252 may be configured to couple to the outer surface 170 proximate the front waist portion 110. The attachment area 252 may be coupled to the outer surface 170 proximate the front edge 112, and may extend a width of the front edge 112. In other embodiments, the flap 200 may be configured to be coupled to the outer surface 170 of the diaper 100 proximate the rear waist portion 130, and may further be coupled proximate the rear edge 132.

It is foreseeable that the flap 200 may be permanently fixed from the attachment end 210 to the outer surface 170 at the front waist portion 110 of the diaper 100. The diaper 100 and flap 200 may be a single, unitary construction. In those embodiments, the attachment area 252 and the outer surface 170 of the diaper 100 may be indistinguishable and the flap 200 may extend from the front edge 112. In this configuration, when in use, the flap 200 may not extend up and over the top 114 of the diaper 100, but may extend downward towards the central portion 150 of the diaper 100.

Figure 6:
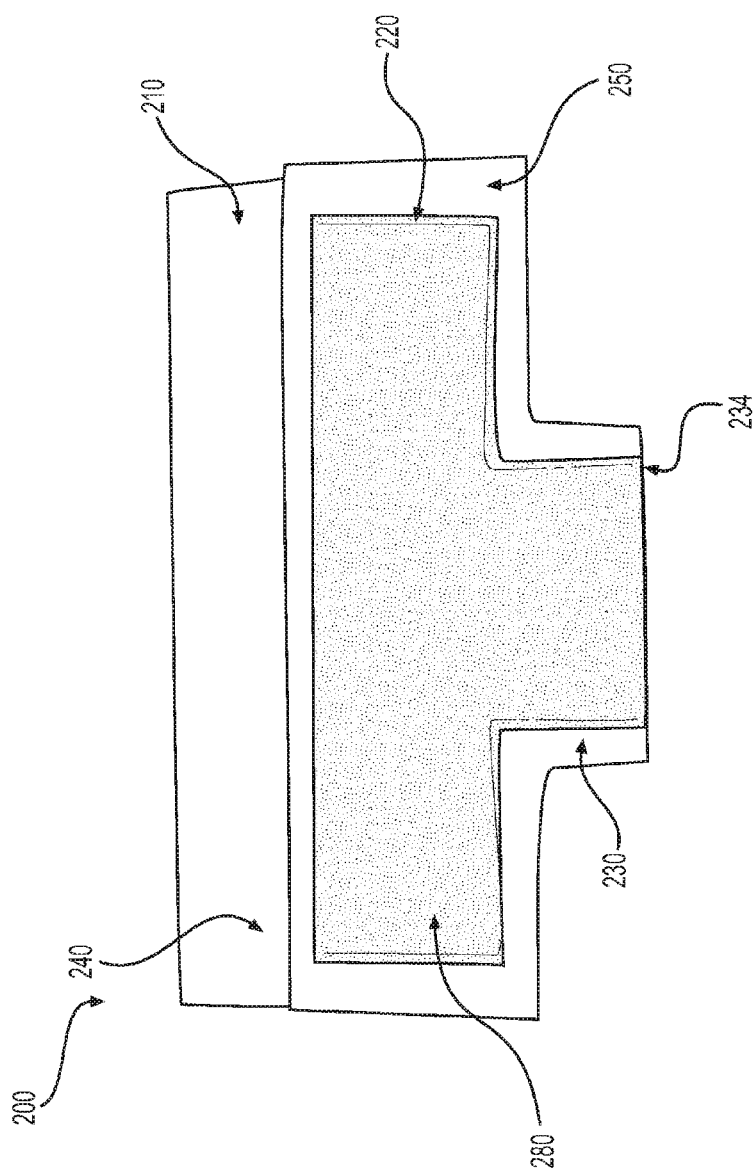
FIG. 6 is a front view of the flap of FIG. 1 in a folded configuration.

The flap 200 may have a planar configuration and a folded configuration (see FIG. 6). The flap 200 may be provided in either configuration. In the folded configuration, the flap 200 may be folded at the midsection 230 forming a folded area 234, which may act as a barrier. The flap 200 may be folded proximate the center point 232 and, the inner surface 250 may be generally exposed, as is shown in FIG. 6. In the folded configuration, the distal end 220 may be proximate the attachment end 210. In some embodiments, the distal end 220 may also be proximate the front edge 112. In the folded configuration and when coupled to the outer surface 170 of the diaper 100, the flap 200 may form a Z-fold, as the flap 200 may be folded at a front edge 112 or rear edge 132 of the diaper 100, and again at the folded area 234. In other embodiments, the flap 200 could further be folded, creating a W-fold, or other accordion type folds.

At least a portion of the inner surface 250 is adjacent to an absorbency area 280. An area of the absorbency area 280 may be more than half an area of the inner surface 250. In some embodiments, the area of the absorbency area 280 may be generally similar (and in some embodiments, identical) to the entire area of the inner surface 250. In other embodiments, the absorbency area 280 may be adjacent to the inner surface 250 except for a boundary of one half inch or less from an outer perimeter 202 of the flap 200 (see FIG. 3). The outer perimeter 202 of the flap 200 may be sealed against leakage such that the absorbency area 280 is secured. The outer perimeter 202 may be crimped, bonded, heat sealed, or sealed with another method now known or later discovered. In some embodiments, the edge of the distal end 224 may be sealed against leakage, and may further have a water impermeable coating. In some embodiments, excess material from the outer surface 240 may extend up and over the edge 224 of the distal end 220 such that the distal end 220 is sealed against leakage. In other embodiments, the absorbency area 280 may be adjacent to the distal end 220 and the midsection 230. A first end of the absorbency area 282 may be proximate the edge of the distal end 222, and a second end 284 may be proximate the boundary of the attachment end 214. In other embodiments, the absorbency area 280 continues into the attachment end 210. A width of the absorbency area 280 at the attachment end 210 may be equal to or less than a width of the absorbency area 280 at the midsection 230.

The absorbency area 280 has at least one absorbent layer 286. The absorbent layer 286 may help to absorb bodily fluids, and may expand and aid in restricting leakage. The absorbent layer 286 is positioned between the attachment end 210 and the distal end 220. The absorbent layer 286 may extend a width of the flap 200. Alternately, the absorbent layer 286 may extend a length of the flap 200. In some embodiments, the absorbent layer 286 extends a width of the distal end 220. The absorbent layer 286 may be configured to expand in an accordion-like fashion.

There may be different numbers of absorbent layers 286 at different parts of the absorbency area 280. In some embodiments, there are additional absorbent layers 286 proximate the distal end 220. In other embodiments, there are additional absorbent layers 286 proximate the midsection 230, and the absorbent layers 286 may be further increased at the folded area 234. The absorbency area 280 may have multiple absorbent layers 286 which may each be composed of a different material. It may be beneficial to have additional absorbent layers 286 at the distal end 220, as well as additional absorbent layers 286 at the midsection 230. Further, there may be additional absorbent layers 286 at a first end 284 of the absorbency area 280. The placement of the absorbent layer 286 may assist in efficiently pushing liquid toward areas that have not yet absorbed liquid. In this regard, the combination of the diaper 100 and the flap 200 may increase the overall efficiency and absorbency when compared to an absorbency of a standard diaper 100. In some embodiments, the absorbent layer 286 may be configured to expand in an accordion-like fashion. Those skilled in the art will appreciate that the absorbent layer 286 may consist of absorbent gel, super absorbent polymers, absorbent fibers, wood pulp, or any other absorbent material now known or later discovered.

Figure 7:
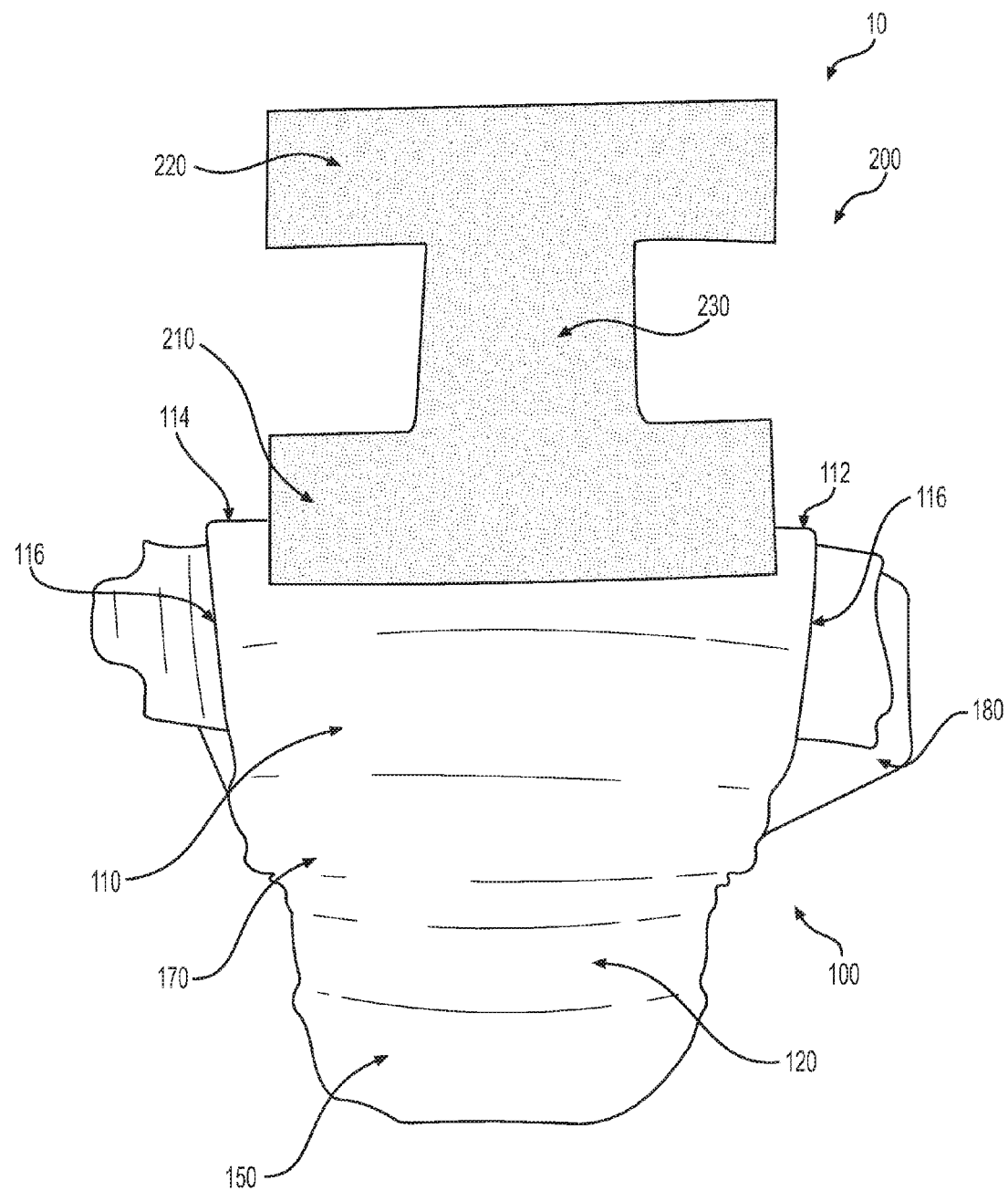
FIG. 7 is a front view of the diaper and the flap of FIG. 1, with the flap coupled to the diaper.
Figure 8:
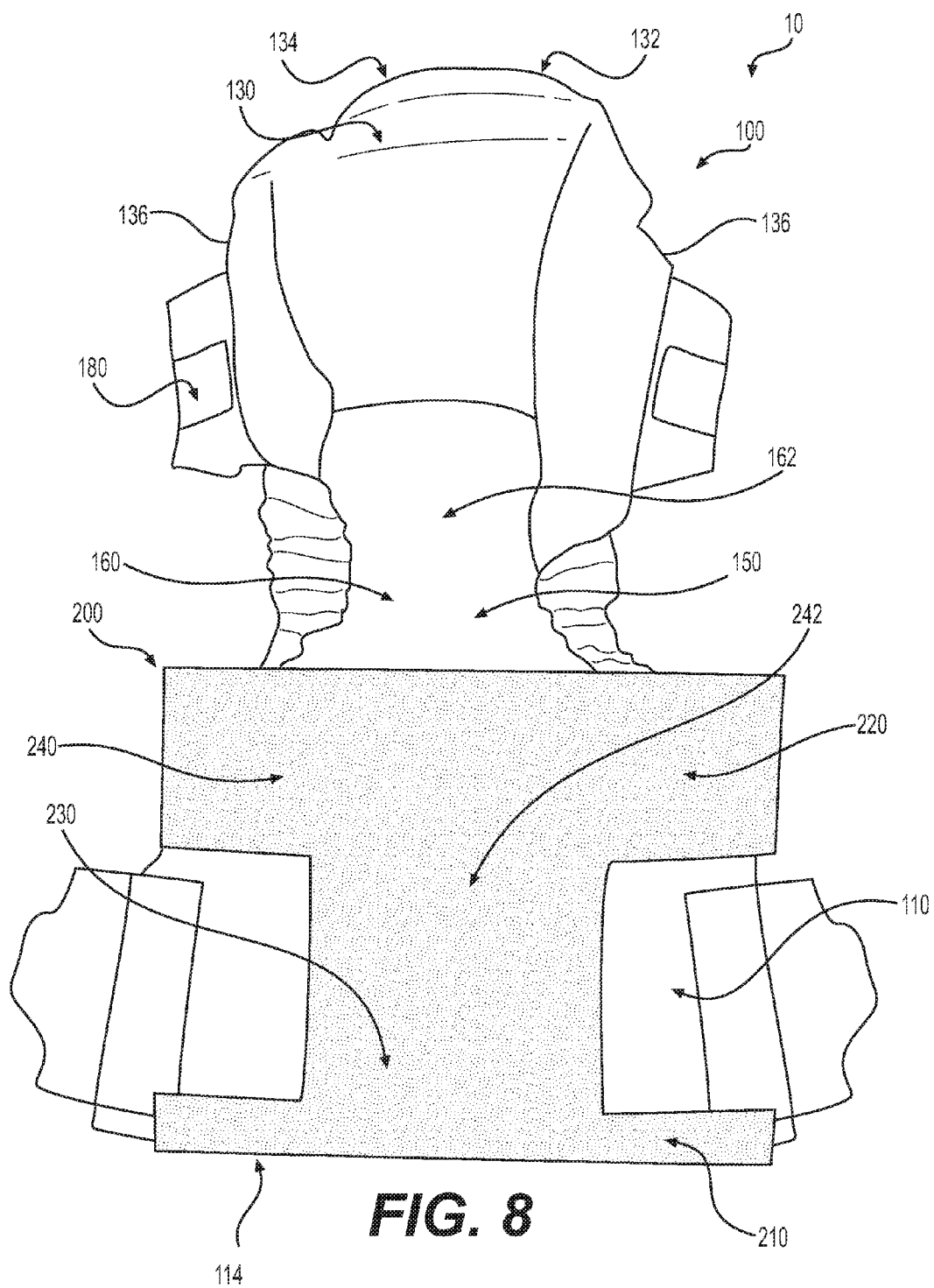
FIG. 8 is a top view of the diaper and the flap of FIG. 1, with the diaper open and the flap folded toward the diaper.
Figure 9:
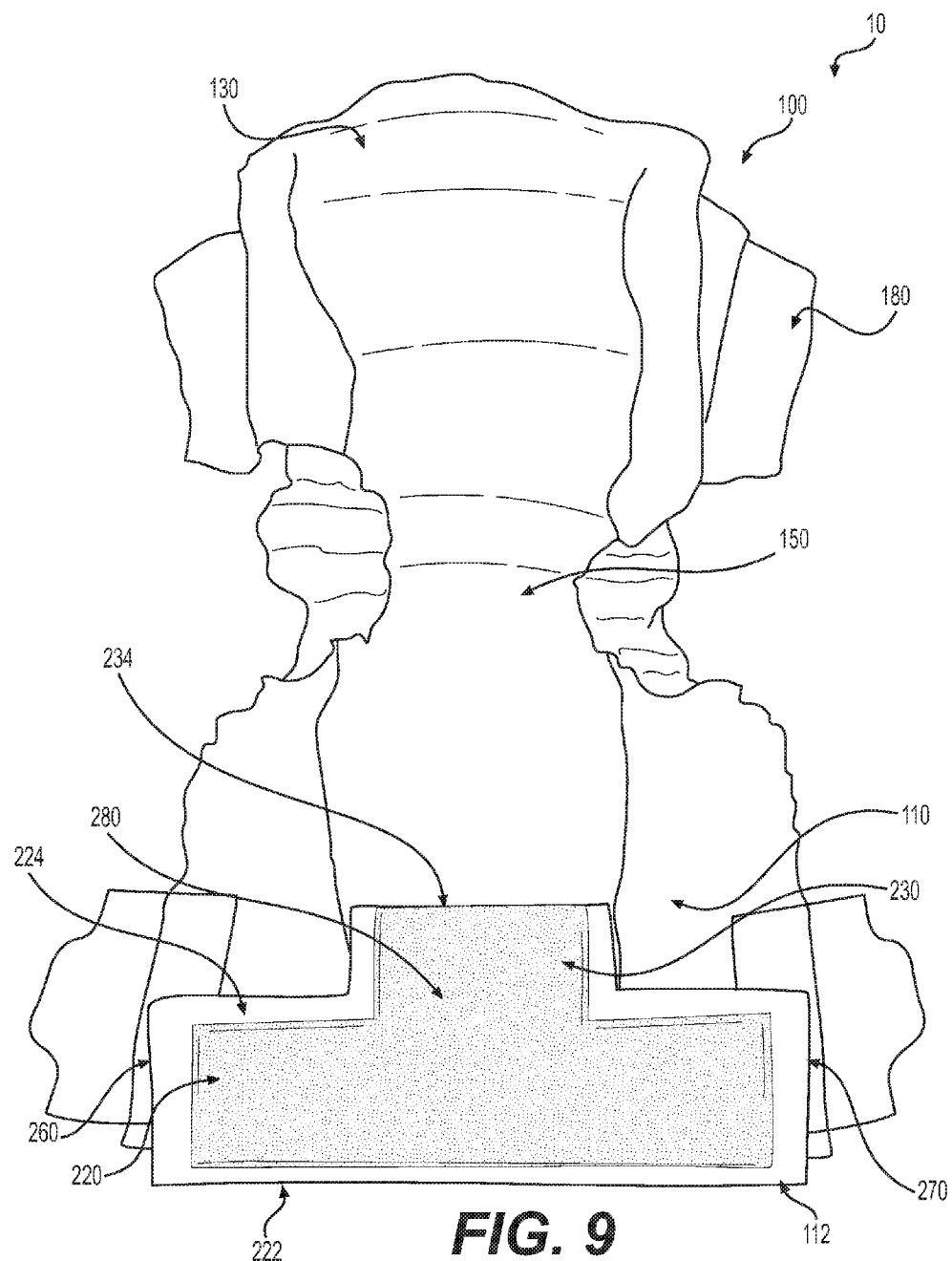
FIG. 9 is a top view of the diaper and the flap of FIG. 1, with the diaper open and the flap at the folded configuration of FIG. 6.
Figure 10:
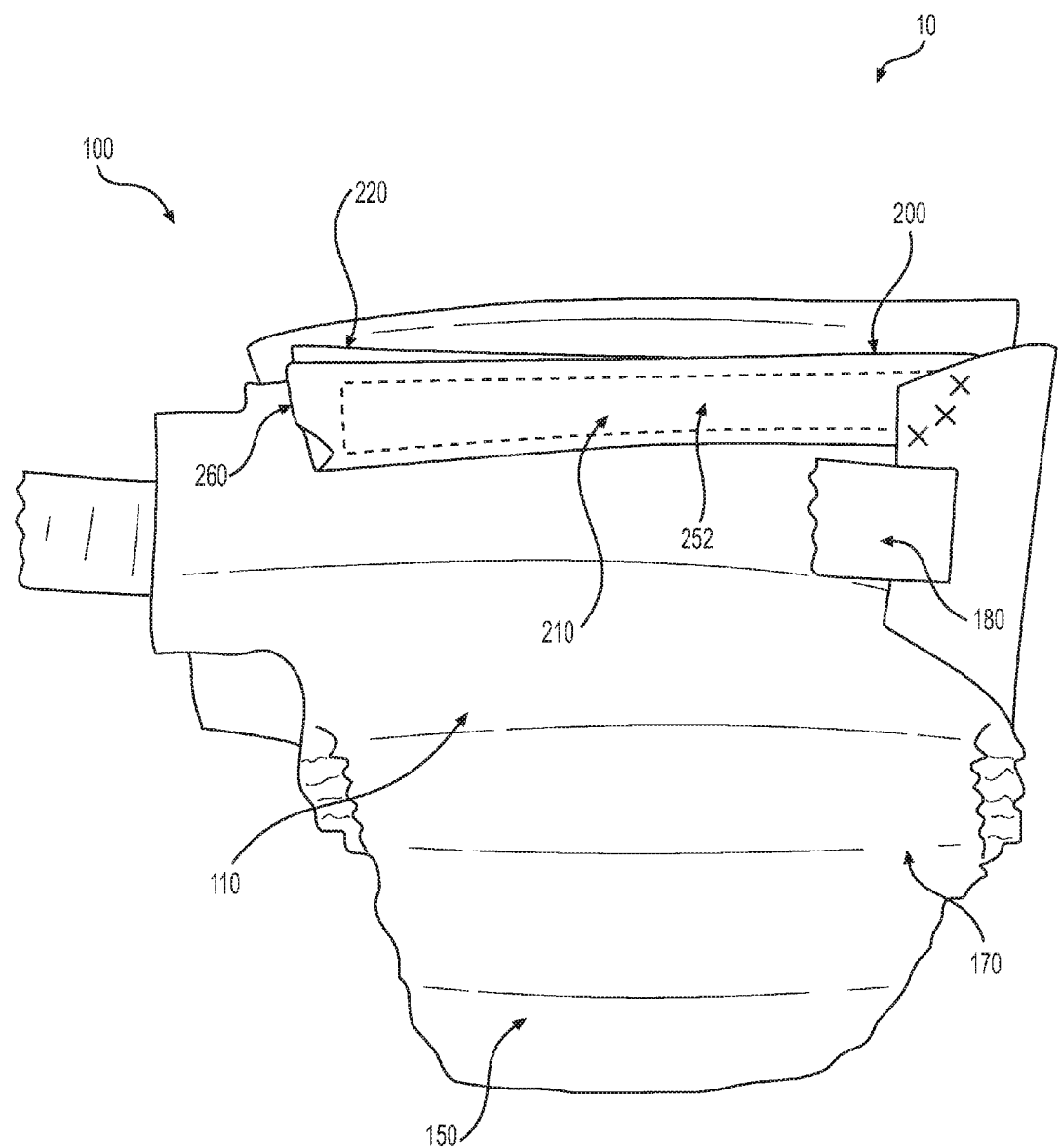
FIG. 10 is a front view of the diaper and the flap of FIG. 1, showing the outer surface of the diaper with the flap folded into the diaper.

In some embodiments, and as shown in FIG. 7, the flap 200 may be configured to be coupled to the outer surface 170 of the diaper 100 proximate the front edge 112. Coupling the flap 200 to the diaper 100 may aid in minimizing leakage. Further, the flap 200 may act as a barrier and provide additional absorbency. The flap 200 may already be in a folded configuration, or the flap 200 may be substantially planar. As shown in FIG. 8, the flap 200 may be coupled proximate the front edge 112, and may then be folded up and over the top 114 of the front waist portion 110 and into the diaper 100, forming a first fold. The flap 200 may extend along the interior surface 160 of the diaper 100 from the front edge 112 to the rear edge 132. If the flap 200 is not in the folded configuration, the flap 200 may then be folded at the midsection 230 to create the folded area 234, as is shown in FIG. 9. In the folded configuration, the distal end 220 may be proximate the attachment end 210, and proximate the front edge 112. The external surface 240 may be secured to itself at the adhesion area 242 to ensure that the folded configuration is maintained. The flap 200 may have a Z-fold, as it may be folded up and over the top 114 of the front waist portion 110, and folded again at the folded area 234. Therefore, the flap 200 may be configured to expand in an accordion-like fashion. The inner surface 250 may be exposed to the wearer. Alternately, the flap 200 may be coupled to the interior surface 160. Once the flap 200 is coupled to the diaper 100 and in the folded configuration, the diaper 100 may be worn by the wearer (see FIG. 10 and FIG. 11, the wearer not shown for clarity).

In some embodiments, the flap 200 is reusable. The absorbency area 280 may be configured to be detached and replaced after each use. Alternately, the absorbent layer 286 may be configured to be detached and replaced after each use. Those skilled in the art can appreciate that the absorbency area 280 may be coupled to the flap 200 with an adhesive material, zipper, hook and loop fasteners, or other methods of attachment now known or later discovered. Alternately, the flap 200 may have an insert (not shown) configured to receive the absorbency area 280.

In some embodiments, the flap 200 may be provided by itself, as it may be beneficial for a user to attach the flap 200 to a diaper 100 instead of purchasing diaper systems 10 that have the flap 200 pre-coupled to the diaper 100. A diaper insert and an undergarment flap are substantially similar to the flap 200 as described above, except they are not coupled to the diaper 100.

When in use, the diaper 100 is secured to the wearer. The front edge 112 may be proximate an abdominal area of the user, and the rear edge 132 may be proximate a lower back of the user. The front waist portion 110 may be secured to the wearer such that the front edge 112 may form a seal with the wearer's abdominal area. Likewise, a rear waist portion 130 may be secured to the wearer such that the rear edge 132 may form a seal with the wearer's lower back. When the diaper 100 is secured to the wearer and the wearer shifts positions, it is foreseeable that the changing positions may cause gaps between the wearer and the diaper 100. For example, if the wearer were to place his legs over his head, or sleep on his stomach, this may cause a gap between the front edge 112 and the wearer. The flap 200 may allow the wearer to move more freely while the diaper system 10 maintains leakage protection.

Figure 11:
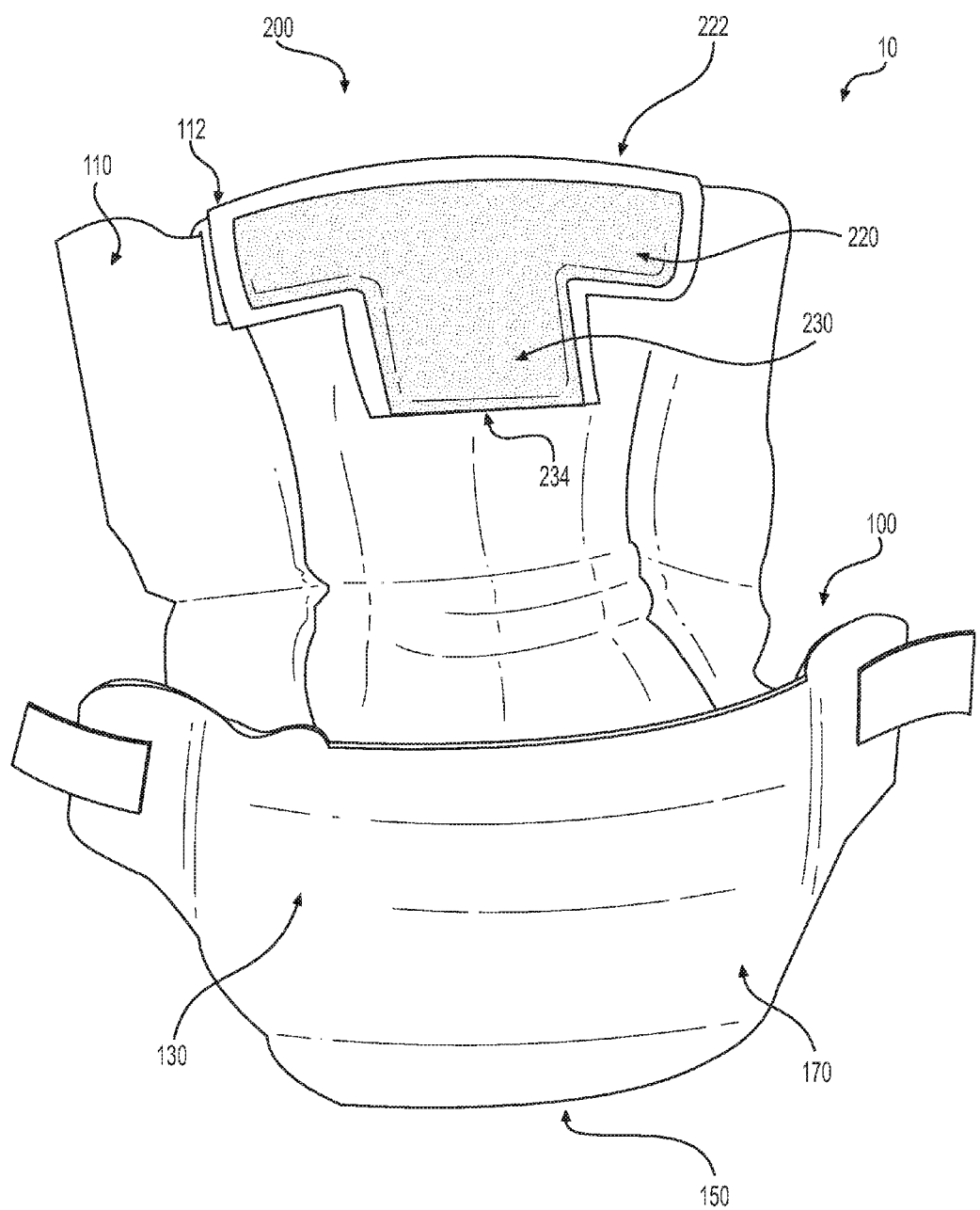
FIG. 11 is top view of FIG. 10, showing an interior of the diaper with the flap coupled to the diaper.

In use, the flap 200 may be attached to the diaper 100 and may be folded at the folded area 234. The folded area 234 may form a barrier between male genitalia of the wearer. The folded area 234 may be positioned below a waist of the wearer. A distal end 220 may be proximate the front edge 112 as shown in FIG. 11, and if the diaper 100 is fastened to the wearer, the front edge 112 may be secured tightly enough to the wearer such that the distal end 220 is held in place proximate the wearer's abdominal area. The distal end 220 may form a barrier proximate the front edge 112 such that fluids may be restricted from flowing upwards and out of the front edge 112 of the diaper 100. Similarly, if the flap 200 is coupled proximate the rear edge 132, the distal end 220 may form a barrier proximate the rear edge 132 such that fluids may be restricted from flowing upwards and out of the rear edge 132 of the diaper 100.

Figure 12:
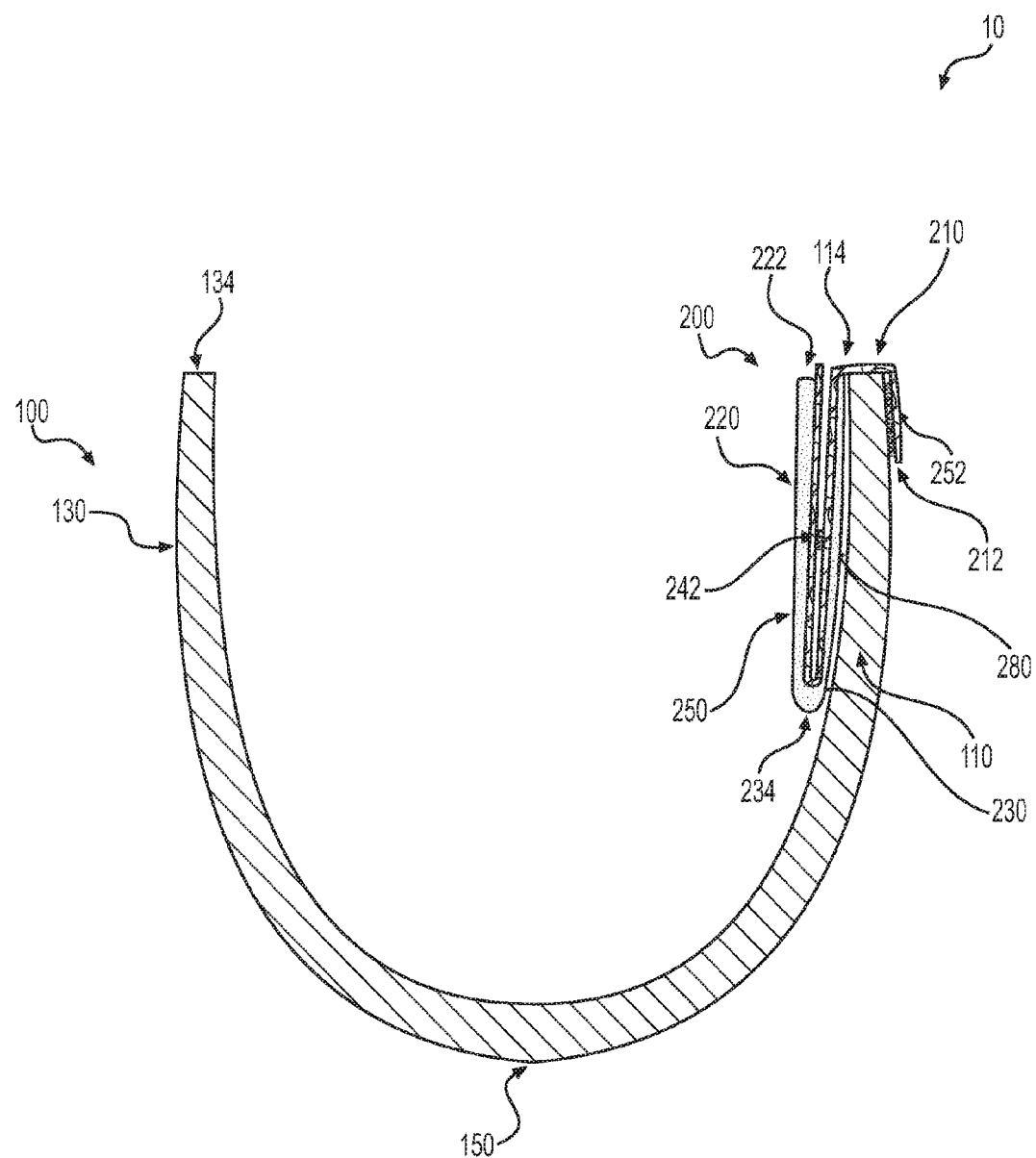
FIG. 12 is a cross sectional view of one embodiment of the diaper and flap of FIG. 1 at a dry use configuration.
Figure 13:
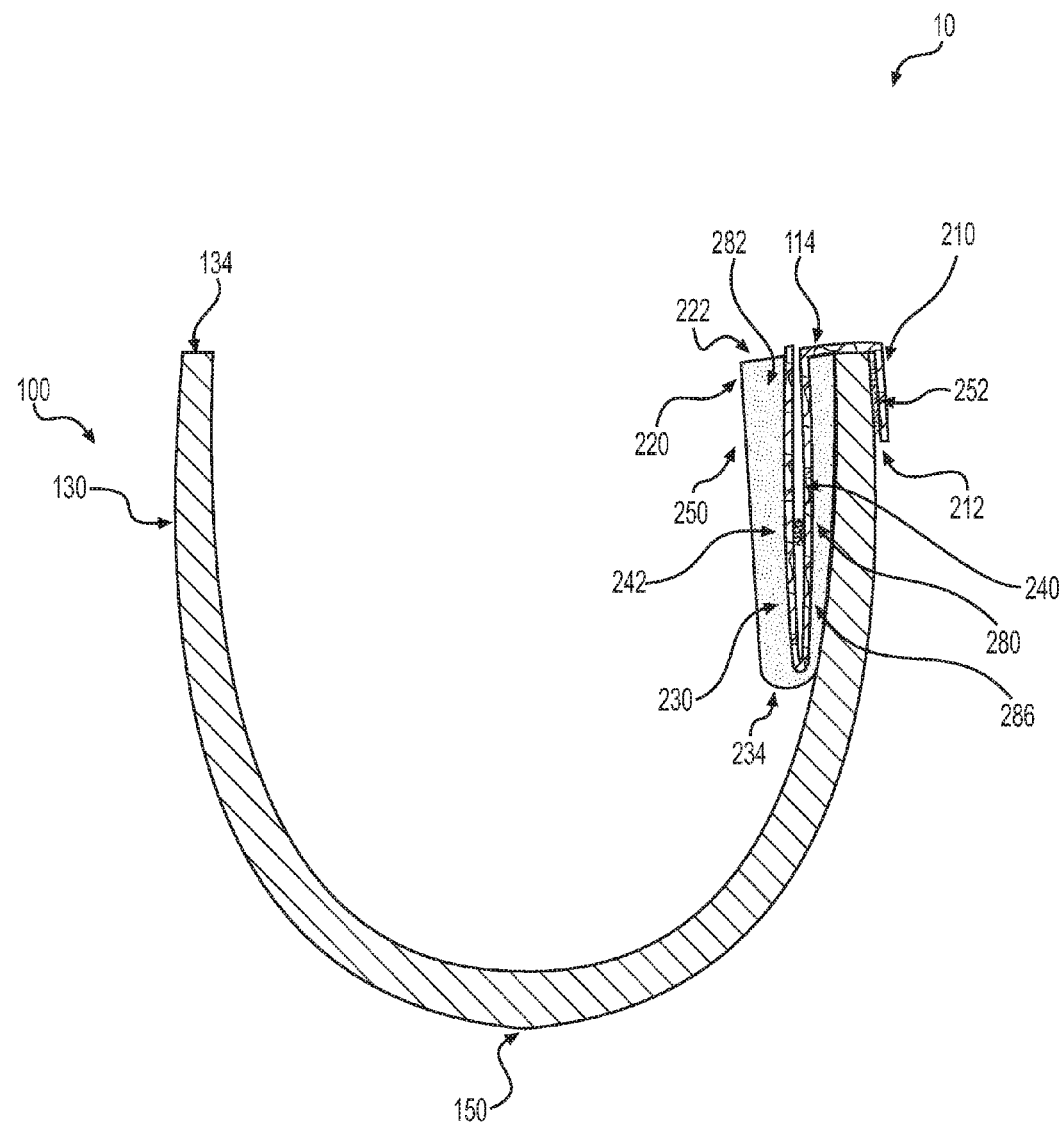
FIG. 13 is a cross sectional view of one embodiment of the diaper and the flap of FIG. 1, with an absorbency area of the flap expanded.

The flap 200 may be used with both male and female users. Male children may more easily urinate towards a front waist portion 110, and the urine may flow over the top 114 and out of the diaper 100. The flap 200 may be positioned to assist in restricting leakage, as is illustrated in FIG. 12. Often, a penis may be pointed in a downward position when a new diaper 100 is put on to attempt to prevent leakage and keep bodily fluids focused towards the central portion 150. However, the penis can easily shift to an upwards position, whereby bodily fluids may flow toward the front waist portion 110. The flap 200 may be positioned to absorb excess liquids proximate the front edge 112 and at the folded area 234. In addition to acting as a barrier, the flap 200 may assist in directing liquid towards areas of the flap 200 and diaper 100 that have not yet absorbed liquid, and may thereby increase the effectiveness of the diaper 100 to absorb liquid. The absorbency area 280 may be configured to receive urine from the wearer that may be relieving his bladder towards a front waist portion 110 of the diaper 100. As is shown in FIG. 13, the absorbency area 280 may expand as it absorbs liquid, and may assist to preventing leakage. The barrier may be formed at the top 114 of the front waist portion 110 of the diaper 100.

Many different arrangements are possible without departing from the spirit and scope of the present invention. Embodiments of the present invention are described herein with the intent to be illustrative rather than restrictive. Alternative embodiments will become apparent to those skilled in the art that do not depart from its scope. A skilled artisan may develop alternative means of implementing the disclosed improvements without departing from the scope of the present invention. Further, it will be understood that certain features and subcombinations are of utility and may be employed without reference to other features and subcombinations and are contemplated within the scope of the invention. The description should not be restricted to the specific described embodiments.

The invention claimed is:

1. An undergarment system, comprising:
    an undergarment, comprising:
        a front waist portion for being positioned proximate a wearer's abdominal area when worn by the wearer, the front waist portion having a front edge;
        a rear waist portion having a rear edge;
        a central portion extending from the front waist portion to the rear waist portion;
        an interior surface;
        an outer surface; and
    a flap having an attachment end, a distal end, a midsection between the attachment end and the distal end, an inner surface, and an external surface; the attachment end being coupled to the outer surface adjacent one of the front and rear edges; an absorbency area adjacent the inner surface having at least one absorbent layer; the midsection having a width that is less than or equal to a width of the distal end;
    said flap being folded along said one of the front and rear edges and extending downwardly along the interior surface, with the at least one absorbent layer of the flap being located substantially entirely below said one of the front and rear edges.

2. The undergarment system of claim 1, wherein the attachment end is coupled to the outer surface proximate the front edge.

3. The undergarment system of claim 1, wherein the attachment end is coupled to the outer surface proximate the rear edge.

4. The undergarment system of claim 1, wherein the flap extends from the front edge toward the rear waist portion.

5. The undergarment system of claim 1, wherein the flap is folded at the midsection.

6. The undergarment system of claim 1, wherein the flap extends from the rear edge toward the front waist portion.

7. The undergarment system of claim 5, wherein:
    the midsection has a center point, and
    the flap is folded proximate the center point such that the flap forms a barrier.

8. The undergarment system of claim 1, wherein the front waist portion, the rear waist portion, and the flap are unitary.

9. The undergarment system of claim 1, wherein:
    the flap extends up and over the front edge toward the central portion; and
    the flap is bent at the midsection and folded such that the distal end is proximate the attachment end.

10. The undergarment system of claim 1, wherein:
    the flap extends up and over the rear edge toward the central portion; and the flap is bent at the midsection and folded such that the distal end is proximate the attachment end.

11. The undergarment system of claim 1, wherein a width of the flap narrows from the distal end toward the midsection.

12. The undergarment system of claim 11, wherein a width of the flap narrows from the attachment end toward the midsection.

13. The undergarment system of claim 1, wherein the attachment end is coupled to the undergarment by at least one fastener selected from the group consisting of: adhesive, pressure sensitive adhesive, hook and loop fasteners, snaps, safety pins, plastic rivets, roll on glue, and a zipper.

14. The undergarment system of claim 1, wherein the flap is "I" shaped.

15. The undergarment system of claim 1, wherein the flap has a fold such that the absorbency area is exposed to the wearer.

16. The undergarment system of claim 1, wherein the flap has a Z-fold configuration.

17. A diaper insert operable to be attached to a diaper including a front waist portion having a front edge, a rear waist portion having a rear edge, an interior surface, and an outer surface, said diaper insert comprising:
    a liquid impermeable external surface;
    an inner surface;
    an absorbency area adjacent the inner surface, the absorbency area having at least one absorbent layer and configured to interact with an inner surface of a diaper to form an absorbent barrier to restrict leakage of bodily fluids;
    a distal end;
    an attachment end configured to be coupled to the outer surface of the diaper adjacent one of the front and rear edges of the diaper;
    a midsection between the attachment end and the distal end, the diaper insert narrowing from the attachment end to the midsection; and
    the midsection having a width that is less than or equal to a width of the distal end,
    said diaper insert being folded along the attachment end to provide an insert fold that extends along said one of the front and rear edges when the attachment end is coupled to the outer surface, so that the at least one absorbent layer extends downwardly along the interior surface and is located substantially entirely below said one of the front and rear edges.

18. The diaper insert of claim 17, wherein:
    the attachment end has opposing sides that are generally parallel to one another; and
    the distal end has opposing sides that are generally parallel to one another.

19. The diaper insert of claim 18, wherein a width of the attachment end is generally equal to a width of the distal end.

20. The diaper insert of claim 19, wherein the midsection has opposing sides that are generally parallel to one another.

21. The diaper insert of claim 17, wherein the diaper insert is folded at the midsection.

22. The diaper insert of claim 21, wherein:
    the midsection has a center point; and
    the diaper insert is folded proximate the center point such that the diaper insert forms a barrier.

23. The diaper insert of claim 17, wherein an attachment area is proximate the attachment end on the inner surface.

24. An undergarment flap operable to be attached to an undergarment including a front waist portion having a front edge, a rear waist portion having a rear edge, an interior surface, and an outer surface, said undergarment flap comprising:
    an external surface;
    an inner surface adjacent an absorbency area;
    at least one absorbent layer adjacent the inner surface;
    an attachment end and a distal end, the attachment end configured to be coupled to the outer surface of the undergarment adjacent one of the front and rear edges of the undergarment; and
    a midsection between the attachment end and the distal end, the midsection having opposing sides that are generally mirror images to one another about a vertical line, a width of the midsection being less than or equal to a width of the attachment end, the width of the midsection being less than or equal to a width of the distal end,
    said undergarment flap being folded along the attachment end to provide a flap fold that extends along said one of the front and rear edges when the attachment end is coupled to the outer surface, so that the at least one absorbent layer extends downwardly along the interior surface and is located substantially entirely below said one of the front and rear edges.

25. The undergarment flap of claim 24, wherein the undergarment flap is folded at the midsection such that the attachment end and the distal end are proximate one another.

26. The undergarment flap of claim 24, wherein the undergarment flap is reusable, and the at least one absorbent layer is configured to be detached and replaced after each use.

27. The undergarment flap of claim 24, further comprising an attachment area located along the inner surface proximate the attachment end, the attachment area having a fastener for coupling to an undergarment.

28. A method for minimizing leakage of bodily fluids from exiting an undergarment system, wherein the method comprises the steps of:
    unfolding an undergarment to be worn by a wearer, the undergarment comprising:
        a front waist portion for being positioned proximate a wearer's abdominal area when worn by the wearer, the front waist portion having a front edge;
        a rear waist portion having a rear edge;
        a central portion extending from the front waist portion to the rear waist portion;
        an interior surface; and
        an outer surface;
    coupling a flap to the outer surface of the undergarment, the flap comprising:
        an attachment end coupled to the outer surface adjacent one of the front and rear edges;
        a distal end;
        a midsection between the attachment end and the distal end;
        an inner surface;
        an external surface; and
        an absorbency area adjacent the inner surface having at least one absorbent layer;
    folding the flap along said one of the front and rear edges up and over into the interior surface of the undergarment to form a first fold, with the at least one absorbent layer being located substantially entirely below said one of the front and rear edges;
    folding the flap at the midsection to create a folded area and an accordion fold, the flap being folded such that the distal end is proximate the attachment end and proximate the undergarment; and securing the undergarment and the flap to the wearer using side fasteners such that the front edge forms a seal with the wearer's abdominal area, and the rear edge forms a seal with the wearer's lower back.

29. The method of claim 28, wherein the attachment end is coupled to the outer surface proximate the front edge, and the flap and the front edge form a seal with the wearer's abdominal area.

30. The method of claim 28, wherein the attachment end is coupled to the outer surface proximate the rear edge, and the flap and the rear edge form a seal with the wearer's lower back.

31. The method of claim 28, wherein the external surface has an adhesion area proximate the midsection and the outer surface is coupled to itself so that a folded configuration of the flap is maintained.

\* \* \* \* \*